(12) United States Patent
Van Der Heide et al.

(10) Patent No.: US 7,456,299 B2
(45) Date of Patent: Nov. 25, 2008

(54) PROCESS FOR THE PRODUCTION OF ALKYLENE CARBONATE AND USE OF ALKYLENE CARBONATE THUS PRODUCED IN THE MANUFACTURE OF AN ALKANE DIOL AND A DIALKYL CARBONATE

(75) Inventors: Evert Van Der Heide, Amsterdam (NL); Gerardus Martinus Maria Van Kessel, Amsterdam (NL); Timothy Michael Nisbet, Amsterdam (NL); Garo Garbis Vaporciyan, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 11/677,997

(22) Filed: Feb. 22, 2007

(65) Prior Publication Data

US 2007/0197802 A1    Aug. 23, 2007

Related U.S. Application Data

(60) Provisional application No. 60/775,636, filed on Feb. 22, 2006.

(51) Int. Cl.
    *C07D 317/08*    (2006.01)
(52) U.S. Cl. .......................... 549/230; 549/229
(58) Field of Classification Search .................. None
    See application file for complete search history.

(56) References Cited

U.S. PATENT DOCUMENTS

| | | | | |
|---|---|---|---|---|
| 2,773,070 | A | 12/1956 | Lichtenwalter | 260/340.2 |
| 2,873,282 | A | 2/1959 | McClellan | 260/340.2 |
| 2,924,608 | A | 2/1960 | Mills | 260/340.2 |
| 2,994,705 | A | 8/1961 | Crosby et al. | 260/340.2 |
| 3,748,345 | A | 7/1973 | Pasquale | 260/340.2 |
| 3,803,201 | A | 4/1974 | Glipin et al. | 260/463 |
| 4,314,945 | A | 2/1982 | McMullen et al. | 260/340.2 |

(Continued)

FOREIGN PATENT DOCUMENTS

CN    1060091    4/1992

(Continued)

OTHER PUBLICATIONS

Synthesis of Propylene Carbonate and Some Dialkyl Carbonates in the Presence of Bifunctional Catalyst Compositions, by Hong Zhu, Bi-Ban Chen and Ying-Yan Jiang, *Polymers for Advanced Technologies*, vol. 7, pp. 701-703.

(Continued)

*Primary Examiner*—Karl J Puttlitz

(57) ABSTRACT

An alkylene carbonate is produced by the reaction of an alkylene oxide with carbon dioxide in the presence of a phosphonium compound as catalyst in a process in which (a) the alkylene oxide, carbon dioxide and the phosphonium catalyst are continuously introduced into a reaction zone from which a product stream containing alkylene carbonate and catalyst is withdrawn, (b) alkylene carbonate and a mixture of alkylene carbonate and phosphonium catalyst are separated from the product stream, (c) the alkylene carbonate, separated in step (b), is recovered as product, and (d) the mixture of alkylene carbonate and phosphonium catalyst is continuously recycled to the reaction zone.

The alkylene carbonate thus produced is suitably reacted with an alkanol to produce an alkane diol and a dialkyl carbonate.

10 Claims, 1 Drawing Sheet

U.S. PATENT DOCUMENTS

| | | | |
|---|---|---|---|
| 4,434,105 A | 2/1984 | Buysch et al. | 260/463 |
| 4,508,927 A | 4/1985 | Bhise et al. | 568/858 |
| 4,691,041 A | 9/1987 | Duranleeau et al. | 558/277 |
| 5,153,333 A | 10/1992 | Schubert et al. | 549/230 |
| 5,231,212 A | 7/1993 | Buysch et al. | 558/277 |
| 5,359,118 A | 10/1994 | Wagner et al. | 558/277 |
| 5,426,207 A | 6/1995 | Harrison et al. | 558/274 |
| 5,449,791 A | 9/1995 | Wagner et al. | 549/230 |
| 5,455,368 A | 10/1995 | Janisch et al. | 58/277 |
| 5,508,442 A | 4/1996 | Wagner et al. | 549/228 |
| 5,847,189 A | 12/1998 | Tojo et al. | 558/277 |
| 6,156,160 A | 12/2000 | Marquis et al. | 203/29 |
| 6,187,972 B1 | 2/2001 | Kawabe et al. | 568/858 |
| 6,294,684 B1 | 9/2001 | de Bruin et al. | 558/274 |
| 6,380,419 B2 | 4/2002 | Kawabe | 558/277 |
| 6,392,078 B1 | 5/2002 | Ryu et al. | 558/277 |
| 6,407,279 B1 | 6/2002 | Buchanana et al. | 558/227 |
| 6,479,689 B1 | 11/2002 | Tojo et al. | 558/277 |
| 6,573,396 B2 | 6/2003 | Buchanan et al. | 558/277 |
| 6,774,256 B2 | 8/2004 | Schlosberg et al. | 558/277 |
| 6,897,343 B2 * | 5/2005 | Von Hebel et al. | 568/867 |
| 2005/0014956 A1 * | 1/2005 | Lange | 549/229 |

FOREIGN PATENT DOCUMENTS

| | | |
|---|---|---|
| CN | 1102826 | 5/1995 |
| CN | 1528735 | 9/2004 |
| EP | 0297647 | 6/1788 |
| EP | 0001082 | 3/1979 |
| EP | 0274953 | 7/1988 |
| EP | 0180387 | 5/1990 |
| EP | 0583789 | 2/1994 |
| EP | 0776890 | 1/2001 |
| EP | 1174406 | 1/2002 |
| EP | 0119840 | 9/2004 |
| JP | 55-64550 | 5/1980 |
| JP | 61-291545 | 12/1986 |
| JP | 2-212456 | 8/1990 |
| JP | 9-183744 | 7/1997 |
| JP | 2000-005503 | 1/2000 |
| JP | 2003-81893 | 3/2003 |
| JP | 2000-113144 | 4/2003 |
| JP | 2003-155264 | 5/2003 |
| JP | 2003-342236 | 12/2003 |
| WO | WO9957108 | 11/1999 |
| WO | WO03006418 | 1/2003 |
| WO | WO03082797 | 10/2003 |
| WO | WO2004/056793 | 7/2004 |
| WO | WO2005003113 | 1/2005 |
| WO | WO2005051939 | 6/2005 |

OTHER PUBLICATIONS

W. J. Peppel, "Preparation and Properties of the Alkylene Carbonates," XP-002396365, Industrial and Engineering Chemistry, vol. 50, No. 5, May 1958, pp. 767-770.

* cited by examiner

US 7,456,299 B2

PROCESS FOR THE PRODUCTION OF ALKYLENE CARBONATE AND USE OF ALKYLENE CARBONATE THUS PRODUCED IN THE MANUFACTURE OF AN ALKANE DIOL AND A DIALKYL CARBONATE

This application claims the benefit of U.S. Provisional Application No. 60/775,636 filed Feb. 22, 2006.

FIELD OF THE INVENTION

The present invention relates to a process for the production of alkylene carbonate and the use of alkylene carbonate thus produced in the manufacture of an alkane diol and a dialkyl carbonate.

BACKGROUND

Processes for the production of alkylene carbonates are known. WO-A 2005/003113 discloses a process in which carbon dioxide is contacted with an alkylene oxide in the presence of a suitable catalyst. The catalyst disclosed is a tetraalkyl phosphonium compound. This specification discloses that the catalyst is very stable if the catalyst is recycled to the alkylene carbonate preparation in an alcohol, in particular in propylene glycol (1,2-propane diol). In WO-A 2005/051939 it is disclosed that the decomposition of such a phosphonium catalyst is reduced if the reaction is conducted in the presence of a minor amount of carbonyl compounds, in particular aldehydes. Both documents show the effectiveness of the processes in batch experiments.

Although the presence of 1,2-propane diol as solvent reduces the decomposition of the phosphonium catalyst, it has the disadvantage that the compound is prone to reaction with the alkylene oxide. This becomes more apparent in the case of a continuous process in which the catalyst is recycled to the reactor where the alkylene carbonate is actually formed. Further, in a continuous process the reaction product containing alkylene carbonate, 1,2-propane diol and catalyst has to be subjected to a work-up treatment. Such work-up treatment generally includes one or more distillation steps to separate the product from the reactants. Since the boiling point of 1,2-propane diol is lower than that of propylene carbonate, 1,2-propane diol is removed from the propylene carbonate during the work-up of the reaction product. Therefore, the stabilizing effect of the 1,2-propane diol disappears during the work-up.

SUMMARY OF THE INVENTION

It has now been found that the catalyst stability is not deteriorated if the recycle of the catalyst in the process is conducted in the presence of the alkylene carbonate.

Accordingly, the present invention provides a process for the production of an alkylene carbonate by the reaction of an alkylene oxide with carbon dioxide in the presence of a phosphonium compound as catalyst in which process (a) the alkylene oxide, carbon dioxide and the phosphonium catalyst are continuously introduced into a reaction zone from which a product stream containing alkylene carbonate and catalyst is withdrawn, (b) alkylene carbonate and a mixture of alkylene carbonate and phosphonium catalyst are separated from the product stream, (c) the alkylene carbonate, separated in step (b), is recovered as product, and (d) the mixture of alkylene carbonate and phosphonium catalyst is continuously recycled to the reaction zone.

DETAILED DESCRIPTION

Figure 1:
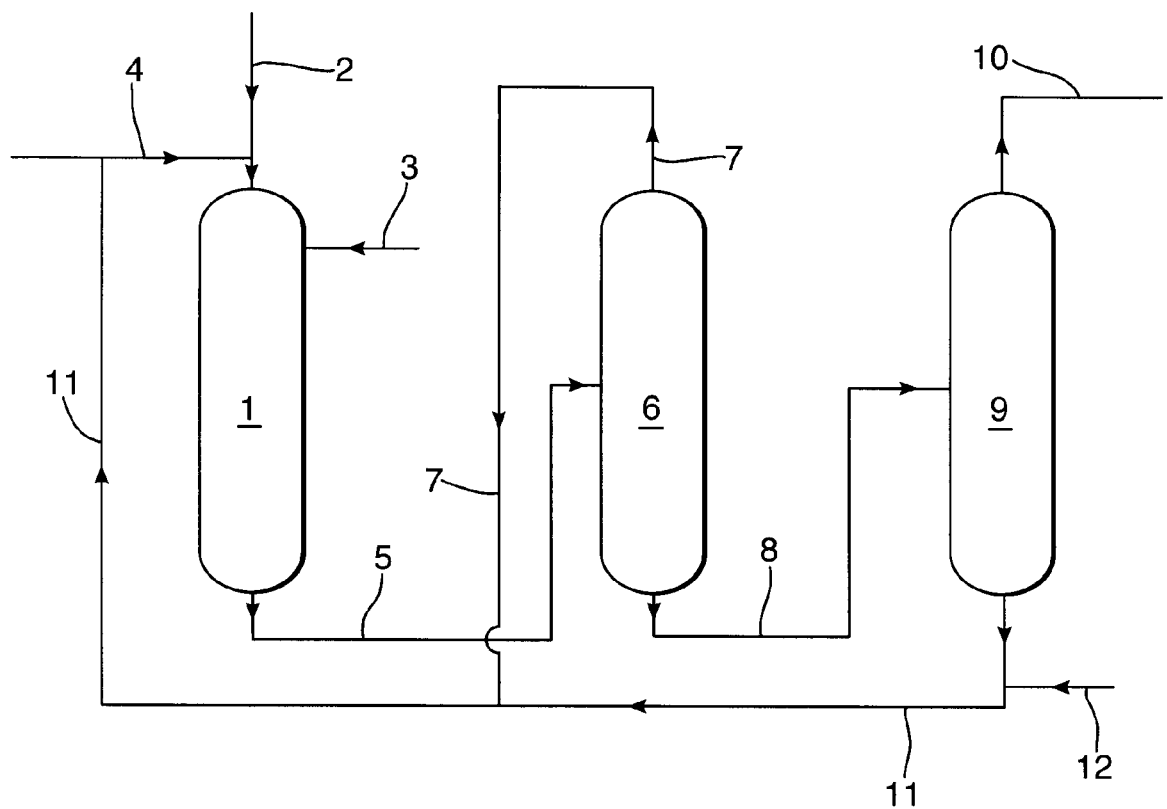
FIG. 1 is a schematic view of the process of the present invention.

The present process allows a long use of the catalyst that is continuously recycled to the reaction zone. It is evident that the process renders a tremendous advantage over the batch processes described in the prior art documents. Because the alkylene carbonate formation is a reversible reaction it would not have been obvious to recycle the alkylene carbonate to the reaction zone since the skilled artisan would have expected a risk of reducing the yield of the desired alkylene carbonate product. Another advantage of the present invention is that since the separation between catalyst and alkylene carbonate does not need to be complete, a relatively inexpensive separation method may be employed.

It has been found that the combination of alkylene carbonate and alkylene oxide may have a deteriorating effect on the catalyst if the catalyst is exposed for a prolonged period to the combination of these compounds. Therefore, it is preferred that the mixture of alkylene carbonate and phosphonium catalyst does not contain more than 1% wt alkylene oxide, preferably at most 0.5% wt, based on the total weight of alkylene carbonate and phosphonium catalyst. Most preferably, the mixture is substantially free of alkylene oxide.

The catalyst is a phosphonium compound. Such catalysts are known, e.g., from U.S. Pat. No. 5,153,333, U.S. Pat. No. 2,994,705, U.S. Pat. No. 4,434,105, WO-A 99/57108, EP-A 776,890 and WO-A 2005/003113. Preferably, the catalyst is a phosphonium halide of formula $R_4PHal$, in which Hal means halide and R can be the same or different and can be selected from an alkyl, alkenyl, cyclic aliphatic or an aromatic group. The group R suitably contains from 1 to 12 carbon atoms. Good results are obtained with R being a $C_{1-8}$ alkyl group. Most preferred are groups R being selected from methyl, ethyl, n-propyl, isopropyl, n-butyl, isobutyl, and t-butyl groups. Preferably, the halide ion is bromide. It appeared that the bromide compounds are more stable than the corresponding chloride compounds and more stable than the corresponding iodide compounds. The most preferred phosphonium catalyst is tetra (n-butyl) phosphonium bromide.

The alkylene oxide that is converted in the present process is suitably a $C_{2-4}$ alkylene oxide, in particular ethylene oxide or propylene oxide or mixtures thereof.

The amount of phosphonium catalyst may conveniently be expressed in moles of catalyst per mole of alkylene oxide. Due to a lower amount of by-products, the subject process is suitably carried out in the presence of at least 0.0001 mole of the phosphonium catalyst per mole of alkylene oxide. Preferably, the amount of phosphonium catalyst present is such that it ranges from 0.0001 to 0.1 mole of phosphonium catalyst, more preferably from 0.001 to 0.05, and most preferably from 0.003 to 0.03 moles of phosphonium catalyst per mole of propylene oxide.

The reaction of carbon dioxide with the alkylene oxide is reversible. That means that the alkylene carbonate formed may convert back into carbon dioxide and the alkylene oxide. The molar ratio between carbon dioxide and alkylene oxide may be as low as 0.5:1, more suitably from 0.75:1. In view of the reversibility of the reaction it is preferred to use an excess of carbon dioxide, such as 1.1:1 to 10:1, more preferably from 1.5:1 to 5:1, most preferably from 1.5:1 to 2:1. A suitable means to establish an excess of carbon dioxide is to conduct the reaction at an elevated carbon dioxide pressure and keeping the pressure constant by dosing carbon dioxide. The total pressure ranges suitably from 5 to 200 bar; the partial carbon dioxide partial pressure is preferably in the range from 5 to 70, more preferably from 7 to 50, and most preferably from 10 to 20 bar.

The reaction temperature can be selected from a wide range. Suitably the temperature is selected from 30 to 300° C. The advantage of relatively high temperature is the increase in reaction rate. However, if the reaction temperature is too high, side reactions, i.e., the degradation of alkylene carbonate to carbon dioxide and propionaldehyde or acetone and the undesired reaction of alkylene oxide with any alkane diol, if present, may occur. Therefore, the temperature is suitably selected from 100 to 220° C.

The skilled person will be able to adapt other reaction conditions as appropriate. The residence time of the alkylene oxide and the carbon dioxide in the reaction zone can be selected without undue burden. The residence time can usually be varied between 5 min and 24 hours, preferably between 10 minutes and 10 hours. Conversion of alkylene oxide is suitably at least 95%, more preferably at least 98%. Dependent on the temperature and pressure the residence time may be adapted. The catalyst concentration may also vary between wide ranges. Suitable concentrations include from 1 to 25% wt, based on the total reaction mixture. Good results can be obtained with a catalyst concentration of 2 to 8% wt, based on the total reaction mixture.

Although the presence of alkylene carbonate already ensures that the stability of the catalyst is maintained, it is preferred to provide for an alcohol in the mixture of alkylene carbonate and phosphonium catalyst. Thereto one may add the alcohol to the mixture before introduction into the reaction zone. Alternatively, one may add the alcohol directly into the reaction zone or in any other suitable place such that the mixture of alkylene carbonate and phosphonium catalyst also contains the alcohol. The alcohol strengthens the stabilizing effect on the phosphonium catalyst at the reaction temperatures. If an alcohol is present the possibility arises that the alcohol reacts with the alkylene oxide to form alkoxy alcohol. That is another reason to keep the reaction temperature relatively low, e.g., in the range of 100 to 220° C.

Many alcohols may be selected to increase the stability of the phosphonium catalyst. The alcohol may be monovalent, bivalent, or multivalent. The alcohol may comprise an aliphatic $C_{1-12}$ chain substituted by one or more hydroxyl groups. Aromatic alcohols or alkylaromatic alcohols may also be used, suitably having 6 to 12 carbon atoms. Polyalkylene glycols or the monoalkyl ethers thereof may also be used. Mixtures may also be used.

Preferably, the alcohols used are selected from the group consisting of $C_{1-6}$ mono-alkanols, $C_{2-6}$ alkane diols, $C_{3-6}$ alkane polyols, including glycerol, phenol, $C_{1-6}$ alkyl substituted phenols, $C_{6-12}$ cycloaliphatic alcohols and mixtures thereof. Very suitable are $C_{2-6}$ alkane polyols, in particular 1,2-ethane diol, 1,2-propane diol, sorbitol and mixtures thereof. The use of ethane or propane diol has the advantage that the reaction mixture is not contaminated with strange alcohols. Sorbitol provides excellent stability to the phosphonium catalyst. It may be advantageous to use a combination of 1,2-ethane or propane diol and sorbitol. When an alcohol is used in the present process the skilled artisan will usually use a molar excess compared to the amount of phosphonium catalyst. However, there is a certain limit. Generally, the alcohol has to be separated from the reaction mixture, in particular from the alkylene carbonate product. For economic reasons the excess will therefore suitably be optimised to balance the benefits as to stability improvement with the costs of separation. Suitably, the amount of alcohol ranges from 1 to 100, preferably from 2 to 60, more preferably from 3 to 15 moles of alcohol per mole of phosphonium catalyst.

As to the relative amounts of alkylene carbonate and alcohol the skilled artisan can vary the ratio in broad ranges. Very good results have been obtained employing a weight ratio of alkylene carbonate to alcohol of 0.1-10, in particular from 0.2 to 5, more preferably from 0.5 to 2. In view of the chance for the undesired reaction between the alkylene oxide and an alcohol in the reaction zone the amount of alcohol is suitably kept at a relatively low level, such as from 1 to 15% wt, based on the weight of alkylene oxide, carbon dioxide, alkylene carbonate and alcohol in the reaction zone. Preferably the amount of alcohol ranges from 5 to 10% wt.

It is advantageous if the content of the phosphonium catalyst in the mixture to be recycled is relatively high. That would mean that the yield of alkylene carbonate product is high whereas the costs for recycle are kept to a minimum. Therefore, the amount of phosphonium catalyst in the mixture of phosphonium catalyst and alkylene carbonate ranges preferably from 1 to 90% wt, based on the total mixture, more preferably from 5 to 75% wt. Since it has been found that the stability of the catalyst is reduced slightly when the alkylene to catalyst weight ratio is below 1 the amount of phosphonium catalyst is most preferably from 10 to 40% wt. The total mixture comprises phosphonium catalyst, alkylene carbonate and, optionally, alcohol.

The alkylene carbonate that is produced in the present process can suitably be used for the production of alkane diol and dialkylcarbonate. Accordingly, the present invention also provides a process for the preparation of alkane diol and dialkyl carbonate comprising reacting an alkanol and alkylene carbonate over a transesterification catalyst in which the alkylene carbonate has been prepared by the process of the present invention, and recovering the alkane diol and the dialkyl carbonate from the resulting reaction mixture. The alkanol is suitably a $C_{1-4}$ alcohol. Preferably the alkanol is methanol, ethanol or isopropanol. The most preferred alkanols are methanol and ethanol.

The transesterification reaction in itself is known. In this context reference is made to U.S. Pat. No. 4,691,041, disclosing a process for the manufacture of ethylene glycol and dimethyl carbonate by the transesterification reaction over a heterogeneous catalyst system, in particular an ion exchange resin with tertiary amine, quaternary ammonium, sulphonic acid and carboxylic acid functional groups, alkali and alkaline earth silicates impregnated into silica and ammonium exchanged zeolites. U.S. Pat. No. 5,359,118 and U.S. Pat. No. 5,231,212 disclose a continuous process for preparing dialkyl carbonates over a range of catalysts, including alkali metal compounds, in particular alkali metal hydroxides or alcoholates, thallium compounds, nitrogen-containing bases such as trialkyl amines, phosphines, stibines, arsenines, sulphur or selenium compounds and tin, titanium or zirconium salts. According to WO-A 2005/003113 the reaction is conducted over heterogeneous catalysts, e.g. alumina. This specification provides in the separation of the phosphonium catalyst from the reaction products. Hereto, it is proposed to remove the phosphonium catalyst together with the alkane diol. However, according to the present invention it is preferred to separate the alcohol, if present, at an earlier stage. According to the present invention the alcohol is preferably separated from the product stream containing alkylene carbonate and phosphonium catalyst. In this way the amount of alcohol to be recycled can be kept to a minimum. Moreover, any halide compound that may be formed during the reaction as by-product is removed from the alkylene carbonate product and cannot hinder any subsequent process step. Further it has been found that if the halide by-product is recycled to the reaction zone together with the alcohol and the phosphonium catalyst they add to the catalytic behavior of the system.

The Figure shows a reaction zone 1 into which alkylene oxide is fed via a line 2. The alkylene oxide is combined with a mixture of phosphonium catalyst, e.g. tetrabutyl phosphonium bromide, via line 4 and together the reactants are passed into the reaction zone 1. The mixture in line 4 also contains an alcohol, e.g. 1,2-propane diol, and alkylene carbonate, e.g. propenyl carbonate. Via a line 3 carbon dioxide is also passed into the reaction zone 1. The reaction zone 1 may comprise only one reactor. It is also feasible to carry out the reaction in two or more reactors. In such cases it may be advantageous to provide for the optimal amount of excess carbon dioxide in the reactors by removing or adding carbon dioxide between the reactors. The reactors are suitably conducted under plug flow conditions. It is even more preferred to have a back-mix reactor, e.g. a Continuously Stirred Tank Reactor (CSTR), followed by a plug-flow reactor. Such a combination is known from e.g. U.S. Pat. No. 4,314,945. From the reaction zone alkylene carbonate together with phosphonium catalyst and the alcohol is discharged from the bottom via a line 5. The contents of line 5 are passed to a first separation zone 6 in which the alcohol is separated via line 7 at the top or alternatively at the upper part, and from which the mixture of alkylene carbonate and phosphonium catalyst is removed via line 8 at the bottom or lower part. From line 7 low-boiling by-products and/or residual excess carbon dioxide may be removed (not shown). It is observed that this situation may arise when the alcohol has a lower boiling point than the alkylene carbonate, as is the case when the alcohol used is 1,2-propane diol and the alkylene carbonate used is propylene carbonate. When a high-boiling alcohol is used in combination with a low-boiling alcohol, e.g. sorbitol in combination with 1,2-propane diol, the effluent in line 8 will comprise the high-boiling alcohol. When only a high-boiling alcohol is used, e.g. only sorbitol in the manufacture of propylene or ethylene carbonate, separation zone 6 needs only to be used for removal of light by-products and/or excess carbon dioxide.

The effluent in line 8 is passed to a further separation zone 9 in which alkylene carbonate is separated, discharged at the top via a line 1, and recovered as product. The bottom product of the separation zone 9 comprises alkylene carbonate, phosphonium catalyst and, optionally, high-boiling alcohol. This bottom product is discharged via line 11. Possibly, make-up alcohol may be added via a line 12 into line 11 or into any other suitable place in the process. At least part of the alcohol that was separated in the separation zone 6 and withdrawn via line 7 is added to the mixture of alkylene carbonate and phosphonium catalyst. The resulting mixture is fed through line 11. Additional make-up catalyst, if any, may be combined with the mixture in line 11 and recycled via lines 4 and 2 to the reaction zone 1.

EXAMPLES

Examples 1

To show that the presence of alkylene carbonate maintains the catalyst stability, a mixture of tetra n-butyl phosphonium bromide catalyst (TBPB), propylene carbonate (PC), and optionally, 1,2-propane diol (1,2PD) was stirred in open air at 120° C. for 18 hours. The catalyst at the start contained 0.06% wt tributyl phosphine oxide (TBPO). The amount of TBPO in the catalyst, as indicative of the degradation of TBPB, was determined after 18 hours via $^{31}$P-NMR. The results are shown in Table 1.

TABLE 1

| Experiment No. | TBPB, g | PC, g | 1,2PD, g | TBPO, % wt |
|---|---|---|---|---|
| 1 | 10 | — | — | 0.21 |
| 2 | 2 | 7.5 | — | 0.26 |
| 3 | 9 | 1 | — | 0.43 |
| 4 | 2 | 6 | 2 | 0.12 |

Example 2

In a series of experiments the effect of liquid on the stability of a phosphonium catalyst was shown.

A mixture of 150 g of propylene carbonate and 50 g tetrabutyl phosphonium bromide was used to mimic a reflux stream from the reaction zone in which propylene oxide is reacted with carbon dioxide. Alcohol (8 g) was added to the mixture and the resulting admixture was kept in a closed vessel at atmospheric pressure and at a specific temperature during a period as indicated in Table 2 below. The degradation of the phosphonium catalyst was determined by $^{31}$P NMR. Also the degradation of the propylene carbonate was determined by measuring the pressure increase at the end of the period. The pressure increase is caused by the decomposition of propylene carbonate to aldehyde and carbon dioxide.

The results are recorded in the Table.

TABLE 2

| Exp. No. | Alcohol | Time, hrs | Temp., ° C. | Catalyst degradation, mol % | Pressure increase, bar |
|---|---|---|---|---|---|
| 5 | — | 172 | 145 | 0.68 | 9 |
| 6 | Glycerol | 172 | 145 | 0.36 | 5.5 |
| 7 | Propanediol | 172 | 145 | 0.41 | 4.5 |
| 8 | Sorbitol | 172 | 145 | 0.35 | 6 |
| 9 | — | 24 | 175 | 1.4 | 20 |
| 10 | Glycerol | 24 | 175 | 0.74 | 9 |

The above results show that the presence of an alcohol in addition to propylene carbonate has a stabilizing effect on the catalyst, and also reduces the degradation of propylene carbonate.

Example 3

This example shows the deleterious effect of propylene oxide on the combination of propylene carbonate and the phosphonium catalyst. Therefore, 50 g of tetra n-butyl phosphonium bromide catalyst (TBPB), 150 g propylene carbonate (PC), 5 g propylene oxide (PO) and optionally, 3 g 1,2-propane diol (1,2PD) were mixed in an autoclave and heated for a certain period at 180° C. The catalyst contained 0.06% wt of tributyl phosphine oxide (TBPO) at the start of the experiment. At the end of the experiment the amount of TBPO was determined by $^{31}$P-NMR. The results are presented in Table 3.

TABLE 3

| Exp. No. | TBPB, g | PC, g | PO, g | 1,2PD, g | Duration, min | TBPO, % wt |
| --- | --- | --- | --- | --- | --- | --- |
| 11 | 50 | 150 | 5 | — | 1350 | 2.50 |
| 12 | 50 | 150 | 5 | 3 | 1300 | 2.37 |

The results show that the combination of propylene oxide and propylene carbonate decreases the stability of the phosphonium catalyst.

The invention claimed is:

1. A process for the production of alkylene carbonate by the reaction of an alkylene oxide with carbon dioxide in the presence of a phosphonium compound as catalyst comprising:
   (a) continuously introducing alkylene oxide, carbon dioxide and phosphonium catalyst into a reaction zone from which a product stream containing alkylene carbonate and catalyst is withdrawn,
   (b) separating alkylene carbonate and a mixture of alkylene carbonate and phosphonium catalyst from the product stream,
   (c) recovering the alkylene carbonate, separated in step (b), as product, and
   (d) continuously recycling the mixture of alkylene carbonate and phosphonium catalyst to the reaction zone.

2. A process according to claim 1, wherein the catalyst is a phosphonium halide of formula $R_4$PHal, in which Hal means halide and R can be the same or different and can be selected from the group consisting of an alkyl, alkenyl, cyclic aliphatic and an aromatic group.

3. A process according to claim 1, wherein the catalyst is tetra (n-butyl) phosphonium bromide.

4. A process according to claim 1, wherein the mixture of alkylene carbonate and phosphonium catalyst further contains an alcohol.

5. A process according to claim 4, wherein the alcohol is selected from the group consisting of $C_{1-6}$ mono-alkanols, $C_{2-6}$ alkane diols, $C_{3-6}$ alkane polyols, phenol, $C_{1-6}$ alkyl substituted phenols, $C_{6-12}$ cycloaliphatic alcohols and mixtures thereof.

6. A process according to claim 5, wherein the alcohol is selected from the group consisting of 1,2-ethane diol, 1,2-propane diol, sorbitol, glycerol and mixtures thereof.

7. A process according to claim 1, wherein the amount of phosphonium catalyst in the mixture of phosphonium catalyst and alkylene carbonate ranges from 1 to 90% wt, based on the total mixture.

8. A process according to claim 1, wherein the mixture of phosphonium catalyst and alkylene carbonate does not contain more than 1% wt alkylene oxide.

9. A process according to claim 8, wherein the mixture of phosphonium catalyst and alkylene carbonate is substantially free of alkylene oxide.

10. A process for the preparation of alkane diol and dialkyl carbonate comprising reacting an alkanol and alkylene carbonate over a transesterification catalyst in which the alkylene carbonate has been prepared by the process according to any one of claims 1 to 9, and recovering the alkane diol and the dialkyl carbonate from the resulting reaction mixture.

* * * * *